United States Patent
Bastioli et al.

(10) Patent No.: US 9,695,105 B2
(45) Date of Patent: Jul. 4, 2017

(54) PROCESS FOR THE PREPARATION OF COMPLEX OLIGOMERIC STRUCTURES

(71) Applicant: NOVAMONT S.P.A., Novara (IT)

(72) Inventors: Catia Bastioli, Novara (IT); Luigi Capuzzi, Novara (IT); Francesca Digioia, Barengo (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 15/124,901

(22) PCT Filed: Mar. 10, 2015

(86) PCT No.: PCT/EP2015/054953
§ 371 (c)(1),
(2) Date: Sep. 9, 2016

(87) PCT Pub. No.: WO2015/135936
PCT Pub. Date: Sep. 17, 2015

(65) Prior Publication Data
US 2017/0022140 A1    Jan. 26, 2017

(30) Foreign Application Priority Data
Mar. 11, 2014 (IT) .............................. MI2014A0375

(51) Int. Cl.
| | | |
|---|---|---|
| *C07C 67/465* | (2006.01) | |
| *C08G 63/16* | (2006.01) | |
| *C08G 63/80* | (2006.01) | |
| *C08G 63/12* | (2006.01) | |
| *C08K 5/103* | (2006.01) | |
| *C07C 67/08* | (2006.01) | |
| *C08G 63/78* | (2006.01) | |

(52) U.S. Cl.
CPC ............ *C07C 67/465* (2013.01); *C07C 67/08* (2013.01); *C08G 63/12* (2013.01); *C08G 63/16* (2013.01); *C08G 63/80* (2013.01); *C08K 5/103* (2013.01); *C08G 63/78* (2013.01)

(58) Field of Classification Search
None
See application file for complete search history.

(56) References Cited

U.S. PATENT DOCUMENTS 1,815,886 A * 7/1931 Bruson .................. C08G 63/06
528/295.5

FOREIGN PATENT DOCUMENTS

| WO | 2008/138892 A1 | 11/2008 |
| WO | 2012/085012 A2 | 6/2012 |
| WO | 2013/189917 A2 | 12/2013 |

* cited by examiner

*Primary Examiner* — Yate K Cutliff
(74) *Attorney, Agent, or Firm* — Polsinelli PC

(57) ABSTRACT

The invention relates to a process to prepare complex oligomeric structures obtained from vegetable oils. The process allows to use a mixture of triglycerides containing dicarboxylic acids produced by the oxidative cleavage of vegetable oils as a starting material, these oils being subjected to a step of heating (condensation) followed by a step of esterification with alcohols at temperatures up to 250° C.

20 Claims, No Drawings

PROCESS FOR THE PREPARATION OF COMPLEX OLIGOMERIC STRUCTURES

CROSS-REFERENCE TO RELATED APPLICATIONS

This application is a National Phase filing under 35 U.S.C. §371 of PCT/EP2015/054953 filed on Mar. 10, 2015; and this application claims priority to Application No. MI2014A000375 filed in Italy on Mar. 11, 2014 under 35 U.S.C. §119. The entire contents of each application are hereby incorporated by reference.

This invention relates to a process for preparing complex oligomeric structures obtained from vegetable oils, the said structures comprising esters containing acid groups which have in turn been esterified.

These structures, characterized by high stability to hydrolysis and thermal oxidation, as well as having high viscosity, are used as a replacement for derivatives of materials of fossil origin and find application as extender oils and additives for rubbers, low pour point high stability lubricants, plasticisers for conventional plastics and bioplastics, polyurethane components, detergent components and bleaching agents, ink components, and monomer units in thermoplastic and thermosetting polymers.

The prospect of increasingly more restricted availability of materials of fossil origin in nature such as petroleum now make it urgent to replace its derivatives with other compounds of natural origin. The requirement to use raw materials from renewable sources to ensure the eco-sustainability of industrial outputs is particularly apparent in the production of consumables, especially in the sectors of plastics, rubber and lubricants.

As far as the plastics industry is concerned, for example, bioplastics in which conventional monomers derived from oil are replaced by raw materials from renewable sources are being developed. With a view to increasing environmental sustainability it is necessary when replacing monomers to look towards increasingly more thorough conversion of present polymer formulations, including the additives used for their processing.

In the field of elastomers it is common practice to use extender oils having a plasticising action derived from the processing of oil to extend the volume of rubbers and thus reduce production costs. The use of these extender oils of mineral origin has disadvantages associated with the high toxicity and carcinogenicity of their components, such as polycyclic aromatic hydrocarbons (PAH).

Even as far as lubricants are concerned, there has long been an increasingly stringent need to replace mineral lubricants with lubricants of renewable origin.

One example of products of natural origin which do not have the disadvantages described above and are at the same time capable of providing functional properties which are substantially similar to those of conventional products of non-renewable origin are the complex oligomeric structures described in international patent application WO 2012/085012 A2.

According to the aforesaid patent application, these complex structures in the nature of esters are prepared from mixtures of triglycerides containing saturated dicarboxylic acids in the presence of monoalcohols through esterification reactions catalysed by strong acids such as for example sulfuric acid or sulfonic acids. However under these reaction conditions problems arise with corrosion and the formation of volatile impurities, which can be avoided in accordance with Italian Patent Application MI2012A001070 by performing the esterification reactions in the absence of catalysts or in the presence of acid catalysts comprising one or more phosphorus compounds.

The two abovementioned patent applications however describe processes characterised by low yields of the product in relation to the weight of the starting triglyceride mixture.

Furthermore, according to the processes in the known art, in order to achieve the characteristics necessary for obtaining the desired product, the starting triglycerides mixture has to undergo various steps of processing and purification. In particular hydrolysis treatments up to temperatures of 300° C. and subsequent distillations to remove a component comprising free carboxylic acids are described. The operations of distilling mono- and dicarboxylic acids are however particularly onerous in that they require high temperature and/or vacuum conditions to be maintained because of the high boiling points of the acids, which may be solid at ambient temperature, depending upon their molecular weights. In view of this, a specific equipment, such as for example thin film evaporator, is also required to reduce the degradative phenomena due to the permanence of the products at high temperatures.

A process has therefore been developed for preparing mixtures of triglycerides comprising the aforesaid complex oligomeric structures which provide high product yields in comparison with the weight of the starting triglycerides mixture and which make it possible to overcome the disadvantages described above.

This process in fact makes it possible to use a mixture of triglycerides containing dicarboxylic acids produced by the oxidative cleavage of vegetable oils as a starting material, these oils being subjected to a step of heating (condensation) followed by a step of esterification with alcohols at temperatures up to 250° C. This process may be performed without the addition of catalysts. In addition to this, the other products of the process are mainly diesters of dicarboxylic acids. Compounds of this type require separation operations which are simpler than those required for mono- and dicarboxylic acids. This brings about appreciable advantages from the point of view of industrial production.

Furthermore these diacid diesters are chemical compounds which are of particular interest for applications in that they can be used directly as monomers in polymerisation reactions.

In particular the object of this invention is a process which provides the steps of:
a) heating an initial mixture of one or more triglycerides containing saturated dicarboxylic acids for a time of at least 10 minutes, obtaining an intermediate mixture comprising the said triglycerides in condensed form and one or more free dicarboxylic acids (condensation step);
b) esterifying the said intermediate mixture with monoalcohols, obtaining a reaction product comprising one or more oligomeric structures and one or more dicarboxylic acid diesters (esterification step);
c) separating the said dicarboxylic acid diesters from the said reaction product, obtaining a mixture of triglycerides comprising one or more oligomeric structures (separation step), in which the said oligomeric structures have the following structure:

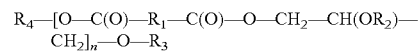

in which
$R_1$ is selected from $C_2$-$C_{22}$ alkylenes,
$R_2$ is selected from one or more of the following groups consisting of $C_6$-$C_{24}$ dicarboxylic acid residues and $C_6$-$C_{24}$ monocarboxylic acid residues, $R_3$ is selected from one or more of the following groups consisting of H, $C_6$-$C_{24}$ dicarboxylic acid residues and $C_6$-$C_{24}$ monocarboxylic acid residues, $R_4$ is an alkyl group, n is a whole number equal to 2 or greater, the said $C_6$-$C_{24}$ $R_2$ and $R_3$ dicarboxylic acid residues being esterified with monoalcohols and the said mixture of triglycerides having a Number Average Molecular Weight (Mn) of between 800 and 10,000 Da.

With reference to the above structure, $R_1$ is preferably a $C_6$-$C_{11}$ alkylene, $C_6$, $C_7$ and/or $C_{11}$ alkylenes being particularly preferred. The two or more $R_1$ in the structure may differ from each other.

$R_2$ represents $C_6$-$C_{24}$ dicarboxylic acid residues or $C_6$-$C_{24}$ monocarboxylic acid residues or a mixture thereof. The two or more $R_2$ in the structure may differ from each other.

$R_3$ represents $C_6$-$C_{24}$ dicarboxylic acid residues or $C_6$-$C_{24}$ monocarboxylic acid residues.

When $R_2$ and/or $R_3$ represent $C_6$-$C_{24}$ dicarboxylic acid residues, the free acid groups of the $C_6$-$C_{24}$ dicarboxylic acid residues are esterified with linear or branched $C_1$-$C_{12}$ monoalcohols. Short chain monoalcohols such as for example methyl alcohol, ethyl alcohol, propyl alcohol and butyl alcohol are particularly preferred. Ethyl alcohol and butyl alcohol are particularly advantageous.

$R_4$ is preferably a linear or branched $C_1$-$C_{12}$ alkyl group, more preferably a $C_2$ or $C_4$ alkyl group.

By $C_6$-$C_{24}$ dicarboxylic acids are meant aliphatic diacids, preferably of the alpha-omega type. Suberic acid, azelaic acid, brassylic acid and their mixtures are particularly preferred.

By $C_6$-$C_{24}$ monocarboxylic acids are meant aliphatic monoacids which may have one or more unsaturations along the chain and which may or may not be substituted.

Preferred unsubstituted monocarboxylic acids are monoacids having a chain length of $C_{9-24}$; palmitic, stearic, oleic, arachidic, behenic and lignoceric acids are particularly preferred.

With reference to the substituted monocarboxylic acids, long chain monocarboxylic acids having one or more ketone groups or hydroxyl groups in non-terminal positions are preferred, and among these $C_{12}$-$C_{24}$ carboxylic acids containing at least one ketone group and $C_{12}$-$C_{24}$ hydroxy acids containing at least one secondary hydroxyl group are particularly preferred. Examples of preferred substituted monocarboxylic acids are 9-hydroxystearic acid, 9-ketostearic acid, 10-ketostearic acid and 10-hydroxystearic acid.

The said substituted monocarboxylic acids may contain two adjacent hydroxyl groups or a hydroxyl group adjacent to a ketone group. If two adjacent hydroxyl groups are present, then dihydroxypalmitic, dihydroxystearic, dihydroxyoleic, dihydroxyarachidic and dihydroxybehenic acids are preferred; 9,10-dihydroxystearic acid is particularly preferred.

Advantageously the oligomeric structures prepared according to the invention are dimer or trimer esters of triglycerides having a repeating units number (n) of 2 or 3.

Dimer and trimer esters of triglycerides containing $C_6$-$C_{24}$ dicarboxylic acid residues are particularly preferred. Examples of preferred dimer and trimer esters are represented by the following structures:

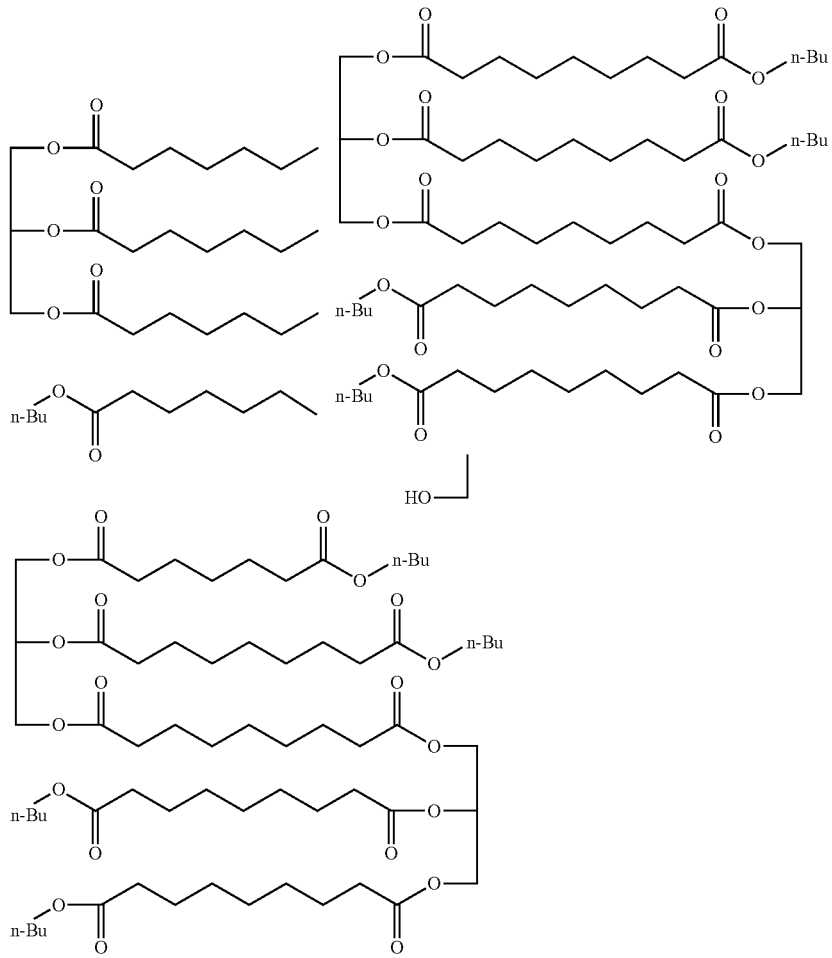

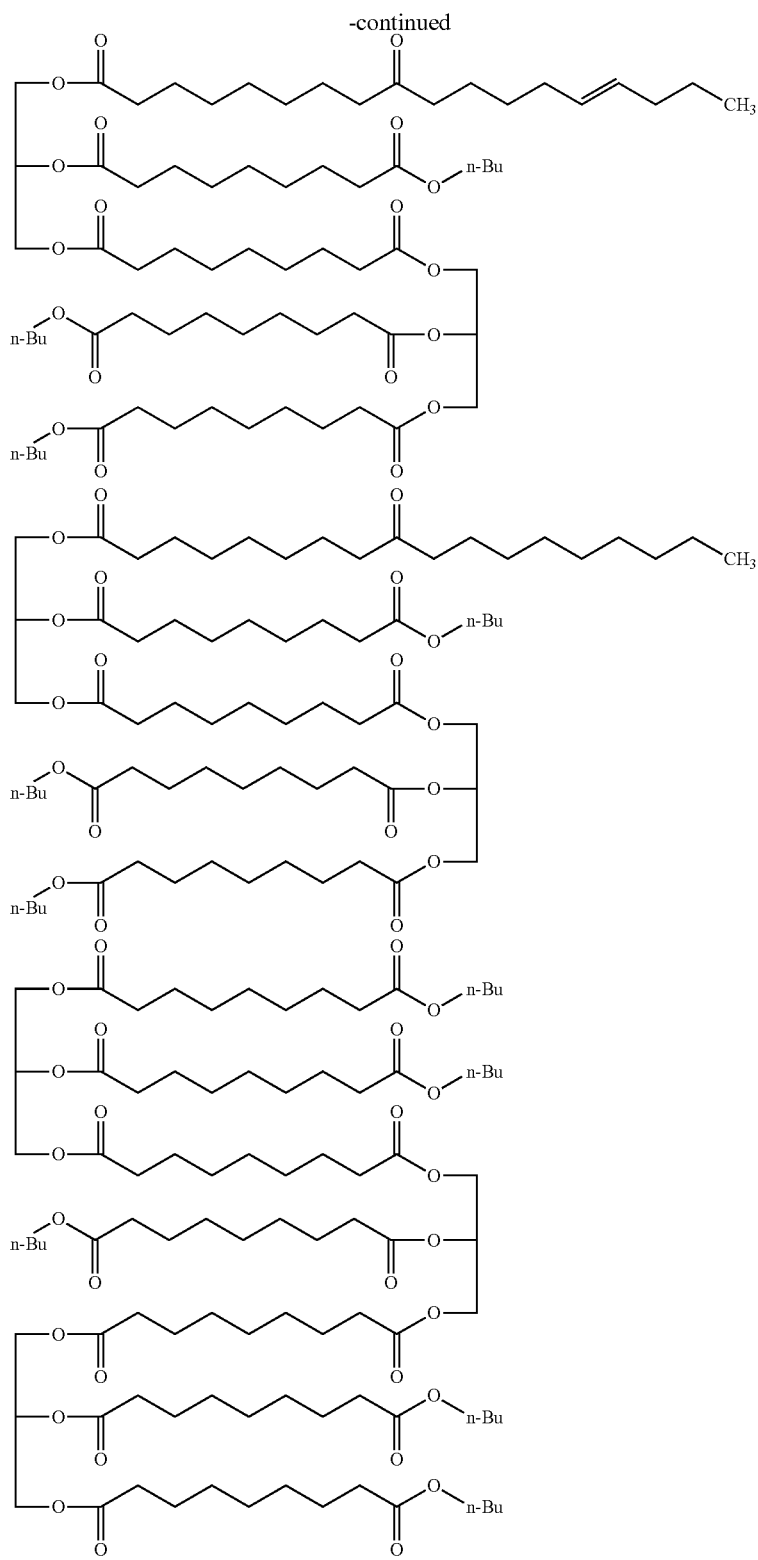

Other examples of oligomeric structures prepared according to the invention have $R_1=C_7$ alkylenes, $R_4=C_4$ alkyls, n=2 and $R_2$ and $R_3$ independently selected from the following groups:

—C(O)—(CH$_2$)$_{6-10}$—COOBu
—C(O)—(CH$_2$)$_{16}$—COOBu
—C(O)—(CH$_2$)$_{6-10}$—CH$_3$
—C(O)—(CH$_2$)$_{16}$—CH$_3$
—C(O)—(CH$_2$)$_{8-9}$—CO—(CH$_2$)$_{7-8}$—CH$_3$
—C(O)—(CH$_2$)$_6$—CO—(CH$_2$)$_7$—CH=CH—CH$_3$.

The mixtures of triglycerides prepared according to this invention may contain monomer triglycerides containing at least one $C_6$-$C_{24}$ dicarboxylic acid residue. Monomer triglycerides containing two $C_6$-$C_{24}$ dicarboxylic acid residues, the said dicarboxylic acids being the same or different, are particularly preferred. Also preferred are monomer triglycerides containing at least one $C_6$-$C_{24}$ dicarboxylic acid residue and at least one $C_6$-$C_{24}$ monocarboxylic acid residue having at least one ketone group and/or at least one hydroxyl group. The dicarboxylic acid residues present in the said monomer triglycerides are esterified with linear or branched $C_1$-$C_{12}$ monoalcohols.

The monomer triglycerides present in the mixtures prepared according to this invention may also contain one or more saturated or unsaturated $C_4$-$C_{24}$ alkyl residues bound to the glycerol molecule through ether links as a replacement for the carboxylic acid residues.

Preferably the mixture of triglycerides prepared according to this invention contains further oligoglycerols such as diglycerol and triglycerol and their esters with mono- or dicarboxylic acids. The said oligoglycerols may contain one or more saturated or unsaturated $C_4$-$C_{24}$ alkyl residues bound to the glycerol molecule through ether links as a replacement for the carboxylic acid residues. Esters of diglycerols and triglycerols comprising one or more $C_6$-$C_{24}$ dicarboxylic acids are preferred. Diglycerol and triglycerol esters comprising at least one saturated or unsaturated monocarboxylic acid residue containing one or more hydroxyl groups and/or a ketone group are also preferred.

Further components of the mixtures of triglycerides prepared according to this invention may be esters of saturated monocarboxylic acids containing one or more secondary ketone and/or hydroxyl groups with linear or branched $C_1$-$C_{12}$ monoalcohols. The said secondary hydroxyl groups may in turn be condensed with monocarboxylic acids and/or dicarboxylic acids and/or alkyl groups. Residues of the said dicarboxylic acids are esterified with linear or branched $C_1$-$C_{12}$ monoalcohols.

In the process for preparing mixtures of triglycerides comprising oligomeric structures according to this invention, the starting mixture of one or more triglycerides containing saturated dicarboxylic acids is obtained from vegetable oils and may contain free $C_4$-$C_{24}$ monocarboxylic acids and $C_6$-$C_{24}$ dicarboxylic acids, triglycerides of $C_6$-$C_{24}$ dicarboxylic acids and $C_4$-$C_{24}$ monocarboxylic acids, di- and triglycerides containing one or more of the following groups consisting of $C_6$-$C_{24}$ dicarboxylic acid residues, $C_4$-$C_{24}$ monocarboxylic acid residues and $C_4$-$C_{24}$ alkyls.

A preferred starting mixture of one or more triglycerides containing saturated dicarboxylic acids is characterised by a Number Average Molecular Weight (Mn) of between 200 and 1000 Da, determined by GPC analysis following calibration with polystyrenes standard. Preferably, the starting mixture has a Number Average Molecular Weight (Mn) of less than 400 Da when measured by GPC analysis after calibration with polystyrene standard.

The starting material for this process is a mixture of triglycerides comprising one or more triglycerides containing at least one dicarboxylic acid, the said dicarboxylic acids being the same or different. The preferred mixture of triglycerides comprises also at least 65%, preferably at least 70%, more preferably at least 75%, even more preferably at least 80% of glycerides of formula $R_x$—O—$CH_2$—CH($OR_y$)—$CH_2$—O—$R_z$, wherein $R_x$, $R_y$, $R_z$ are independently selected from the group consisting of H, $C_6$-$C_{24}$ monocarboxylic acid residues and $C_6$-$C_{24}$ dicarboxylic acid residues, and wherein at least one, preferably at least two of $R_x$, $R_y$, $R_z$ are $C_6$-$C_{24}$ dicarboxylic acid residues.

By $C_6$-$C_{24}$ dicarboxylic acids are meant aliphatic diacids, preferably of the alpha-omega type. Suberic acid, azelaic acid, brassylic acid and their mixtures are particularly preferred.

By $C_6$-$C_{24}$ monocarboxylic acids are meant aliphatic monoacids which may be saturated or unsaturated and substituted or unsubstituted.

Preferred unsubstituted monocarboxylic acids are monoacids having a chain length of $C_{9-24}$; palmitic, stearic, oleic, arachidic, behenic and lignoceric acids are particularly preferred.

When substituted monocarboxylic acid residues are present, long chain monocarboxylic acids having one or more ketone groups and/or hydroxyl groups in non-terminal positions are preferred, and among these $C_{12}$-$C_{24}$ hydroxy acids containing at least one secondary hydroxyl group are particularly preferred. Examples of substituted monocarboxylic acids which may be present are 9-hydroxystearic acid, 9-ketostearic acid, 10-ketostearic acid, 10-hydroxystearic acid, dihydroxypalmitic acid, dihydroxystearic acid, dihydroxyoleic acid, dihydroxyarachidic acid and dihydroxybehenic acid.

The content of glycerides with carboxylic acid residues bearing keto groups is preferably below 10% (HPLC-MS area). According to a preferred embodiment, the said mixture comprises less than 5% of glycerides with carboxylic acid residues bearing keto groups.

The percentage content of the above mentioned glycerides is intended as the % area measured by HPLC-MS analysis operating in gradient mode with ESI (+/−) ionization, using a Mass Spectrometer equipped with a Kinetex Phenomenex 2.6 μm C8 100Å 100×2.1 mm column at 40° C. and PDA detector, with Formic acid 1% (A) and $CH_3CN$ (B) as solvent and the following gradient: 0 min (A/B=80/20), 2 min (A/B=80/20), 40 min (A/B=5/95), 50 min (A/B=5/95), 55 min (A/B=80/20); flow 0.5 ml/min; Full scan 100-2000 Da.

The density of the said starting mixture, determined by weighing 100 mL of the said mixture at a temperature of 100° C., preferably lies between 0.95 and 1.05 g/cm$^3$.

Preferably the kinematic viscosity of the said starting mixture calculated as the ratio between the dynamic viscosity (measured using a HAAKE VT 500 rotary viscometer provided with a MV1 rotor at 100° C.) and density lies between 50 and 1500 cSt.

The said starting mixture preferably has an Acid Value of between 50 and 300 mg of KOH/g. By Acid Value is meant the quantity of KOH expressed in mg required to neutralise the acidity of 1 g of substance. The determination is performed according to standard ASTM D 974-07 in the presence of phenolphthalein.

The degree of unsaturation of the starting mixture, expressed by the $I_2$ Number and determined by titration according to the Wijs method, preferably lies between 0 and 150 g $I_2$/100 g.

The Saponification Number, understood as the quantity of KOH expressed in mg consumed in the saponification of 1 gram of substance, preferably lies between 100 and 450 mg KOH/g.

This is determined by titration with HCl of the residual KOH after reflux saponification for 60 minutes, in the presence of phenolphthalein.

The Hydroxyl Number of the starting mixture, understood as the quantity of potassium hydroxide equivalent to the acetylable hydroxyls in 1 gram of substance, preferably lies between 10 and 100 mg KOH/g. This is determined in accordance with standard ASTM D1957-86.

According to this invention the starting mixture of one or more triglycerides containing saturated dicarboxylic acids is the product of the oxidative cleavage of vegetable oils carried out in batch or continuous mode. One example is the mixture of triglycerides obtained according to the process described in patent application WO 2008/138892 after the monocarboxylic acids have been separated out. Another example is the mixture of triglycerides containing carboxylic acids with more than one acid functional group obtained during the continuous process of oxidative cleavage described in patent application WO 2011/080296. Use of the mixture of triglycerides obtained at the end of step c) in the aforesaid processes (i.e. separation of the saturated monocarboxylic acids) is particularly preferred. By subjecting such starting mixture to heating and subsequent esterification according to this process for the preparation of complex oligomeric structures, decisively higher yields of product are in fact obtained in comparison with the preparations described in the known art. The mixtures of glycerides obtained by the oxidation of sunflower oil and in particular sunflower oil having a high oleic acid content (HOSO, High Oleic Sunflower Oil) are of particular interest as starting mixtures. The process for the preparation of the aforesaid oligomeric structures according to the invention will now be described in detail.

With reference to condensation step (a) according to this invention, the mixture of one or more triglycerides containing dicarboxylic acids is subjected to temperatures preferably comprised between 70 and 250° C., more preferably between 190 and 240° C. and even more preferably between 200 and 240° C. Step (a) may be performed at pressures preferably in the range of between 20 mbar to 2000 mbar, preferably of between 50 mbar to 1500 mbar.

According to a particularly preferred embodiment, step (a) is performed at pressures of between 100 to 250 mbar, more preferably of 150 to 230 mbar.

According to another preferred embodiment, step (a) is performed at pressures in the range of between 600 to 1400 mbar, preferably 400 to 1200 mbar, under flow of air or inert gas (such as nitrogen).

According to another preferred embodiment, the pressure is gradually reduced during step (a). Heating preferably takes place in a reactor heated by means of heat transfer oil, in a flow of nitrogen or air and with vigorous stirring, until the formation of water is observed.

The reaction time is of at least 10 minutes, preferably of between 15 minutes and 17 hours, more preferably between 20 minutes and 1 hour.

The water which forms in the course of the reaction is at least partially removed during condensation step (a), together with the water possibly present in the starting mixture. In the situation where the mixture of triglycerides obtained by one of the processes for the oxidative cleavage of vegetable oils described above is used as the starting mixture, any residual monocarboxylic acids present therein can be further removed.

During the step of condensation according to the invention an intermediate mixture comprising one or more triglycerides containing saturated dicarboxylic acids in condensed form (e.g. dimers and trimers) and one or more free dicarboxylic acids are formed. The terminal free acid groups of the carboxylic acids present in this mixture are subsequently esterified with alcohols in step (b) of the process according to this invention.

As far as the monoalcohols used in step (b) of the process according to this invention are concerned, aliphatic, linear or branched $C_1$-$C_{12}$ alcohols are meant. Short chain linear alcohols such as for example methyl alcohol, ethyl alcohol, propyl alcohol and butyl alcohol are particularly preferred. Ethyl alcohol and butyl alcohol are particularly advantageous.

Advantageously, the said alcohols are added gradually during the reaction.

The water which forms in the course of the esterification reaction is removed until the reaction is complete.

At the end of the reaction the excess alcohol and any volatile esters which may be present can be separated out from the esterification product, preferably by evaporation under vacuum or by distillation.

According to a preferred aspect of this invention the said esterification step (b) is performed without added catalysts. As a result of the acidity of the reaction mixture obtained in step (a) there is in fact obtained the appreciable advantage that step (b) of the process can be performed without it being necessary to add esterification catalysts.

The reaction is preferably performed by heating the esterification reactor to a temperature of preferably less than 250° C.

Esterification temperatures preferably lie between 100 and 250° C., more preferably between 150 and 245° C., even more preferably between 185 and 240° C.

When it is decided to perform this step (b) in the presence of an esterification catalyst, the addition of acid catalysts comprising one or more phosphorus compounds is preferable.

In this case the esterification step requires lower reaction temperatures. By acid catalysts comprising one or more phosphorus compounds are meant mineral acids comprising phosphorus, such as for example the oxyacids, their organic derivatives in which the acid is esterified with alcohols, or their mixtures.

Examples of phosphorus oxyacids suitable for catalysing the process according to the invention are phosphoric or orthophosphoric acids, phosphonic acid, oligo- or polyphosphoric acids, condensation products of phosphoric acid, or their mixtures. The condensation products of phosphoric acid may be linear (for example pyrophosphoric acid, tripolyphosphoric acid, tetrapolyphosphoric acid), cyclic (such as for example trimetaphosphoric acid) or branched. The use of orthophosphoric acid is particularly advantageous.

Esters of such mineral acids containing phosphorus, in particular the esters or phosphates obtained by condensation with short chain alcohols, are also suitable for catalysing esterification reactions according to this invention. Among the phosphoric esters or phosphates, mono-, di- or triesters having short chain alkyl radicals such as for example the methyl, ethyl, propyl and butyl groups are preferred. Catalysts comprising ethylated or butylated phosphates are particularly preferred.

In the case where the reaction is performed in the presence of an acid catalyst comprising one or more phosphorus compounds, the reaction is preferably performed by heating the esterification reaction to temperatures of between 50 and 200° C., more preferably between 60 and 180° C., even more preferably between 80 and 140° C. Preferably the reaction is performed by removing the water which forms in the course of the reaction, for example by evaporation under vacuum. The esterification product may be purified to remove the acid catalyst; the excess alcohol and volatile esters can therefore be separated out, preferably by evaporation under vacuum.

The catalyst may for example be removed by washing with water or basic solutions, for example aqueous solutions of sodium bicarbonate. If phosphoric acid is used, the catalyst is advantageously removed by washing with distilled water alone.

The reaction product obtained in step (b) of the process mainly comprises a mixture of triglycerides comprising one or more oligomeric structures and one or more dicarboxylic acid diesters.

The presence of the said oligomeric structures may be determined by different analytical methods well known to those skilled in the art, such as chromatographic methods combined with mass spectrometry, e.g. LC/MS.

The dicarboxylic acid diesters are separated from the reaction product obtained in step (b) during step (c) of the process according to this invention.

Separation step (c) may be performed using known techniques. Separation by distillation or by evaporation under vacuum in a falling film or thin film evaporator is particularly preferred. Thanks to the peculiar composition of the starting mixture of triglycerides, the weight ratio of the resulting mixture of triglycerides containing oligomeric structures according to the invention and the evaporated volatile butyl esters fraction is advantageously higher than 60/40 (v/w), more advantageously higher than 65/35 and even more advantageously higher than 70/30.

The mixtures of triglycerides comprising oligomeric structures prepared according to the invention preferably have a kinematic viscosity of between 5 and 400 cSt at 100° C., determined as described above.

The glass transition temperature (Tg) of the triglyceride mixtures prepared according to the invention preferably lies between −85° C. and −40° C., more preferably between −80° C. and −50° C. and even more preferably between −73° C. and −60° C. These Tg values make the mixtures which can be derived from vegetable oils prepared according to the invention particularly suitable for use in elastomer compositions as a replacement for conventional extender oils.

The glass transition temperature (Tg) is determined by Scanning Differential calorimetry in a single pass from −100° C. to 30° C. with a rate of temperature change of 20° C./min.

The mixtures of triglycerides comprising oligomeric structures prepared according to this invention preferably have a density of between 0.90 and 1.05 g/cm$^3$ (T=100° C.).

Advantageously, the Acid Value of the product is less than 50, preferably less than 10 and more preferably less than 5 mg KOH/g.

According to a preferred aspect the mixtures of triglycerides comprising oligomeric structures have an $I_2$ Number of between 0 and 140 g $I_2$/100 g.

The Saponification Number of the triglyceride mixtures containing oligomeric structures is preferably between 150 and 500 mg KOH/g.

The Hydroxyl Number of the triglyceride mixtures preferably remains between 10 and 100 mg KOH/g.

The mixtures of triglycerides prepared according to this invention are insoluble in boiling water. These mixtures are however completely soluble in diethyl ether, ethyl alcohol, acetone and chloroform at ambient temperature. They are also characterised by high stability to hydrolysis.

The process for the preparation of mixtures of triglycerides containing complex oligomeric structures according to the invention will now be described on the basis of a non-limiting example.

EXAMPLES

Characterisation of the Product

Molecular Masses were determined by Gel Permeation Chromatography (GPC) using an Agilent 1100 liquid chromatograph equipped with three 5 μm PL gel columns connected in series having a porosity of 10E4, 10E3 and 500 Angstrom (Å). Chloroform at a flow rate of 1 mL/min was used as the eluent. The calibration curve was constructed using standard polystyrenes. The temperature of the column was set at 40° C. The samples were dissolved in chloroform (0.15 mg/ml) and filtered through Teflon filters (pore diameter: 0.20 μm).

Example 1

The mixture of triglycerides containing dicarboxylic acids obtained during the process of oxidative cleavage of sunflower oil described in patent application WO 2011/080296 after step c) of separating out pelargonic acid was used as the starting mixture. The HPLC-MS analysis of the mixture of triglycerides revealed the presence of 94% (area) of glycerides of formula $R_x$—O—$CH_2$—CH(OR)$_y$)—$CH_2$—O—$R_z$, according to the invention, wherein at least one of $R_x$, $R_y$ and/or $R_z$ is azelaic acid. The kinematic viscosity of the triglycerides mixture at 100° C. was 86.8 cSt.

Step (a)-condensation 1243 g of the mixture of triglycerides containing dicarboxylic acids was placed in a glass reactor heated by means of a heat transfer oil bath and provided with a mechanical stirrer, a tube for inserting a flow of gas, a thermometer and a condenser.

The reaction mixture was heated to 230° C. for 30 minutes under a flow of nitrogen removing the water formed and light monocarboxylic acids present.

Step (b)-esterification

After heating, the reaction mixture was cooled and when it reached an internal temperature of 180° C. the gradual addition of butyl alcohol by means of a peristaltic pump (or drip funnel) was begun.

The esterification reaction was performed by heating the reaction mixture under reflux and removing the water by means of azeotropic distillation. 255 g of butyl alcohol were added.

Step (c)-separation of dibutyl azelate

The excess butyl alcohol and the volatile butyl esters were separated off by evaporation under vacuum (pressure=5 mbar and vapour T between 80 and 250° C.). 1069 g of a mixture of triglycerides containing oligomeric structures was obtained. The weight ratio of the resulting mixture of triglycerides containing oligomeric structures to the evaporated volatile butyl esters fraction was of about 75/25.

The Mn for the mixture of triglycerides containing oligomeric structures prepared by the esterification reaction according to the invention was 1886 Da.

Comparative Example 1

A mixture of triglycerides containing oligomeric structures was prepared according to Example 1 of the patent application WO 2012/085012 by esterification with butyl alcohol.

The HPLC-MS analysis of the mixture of triglycerides after evaporation of the free carboxylic acids in a thin film evaporator (residence time 120 seconds) revealed the presence of 43% (area) of glycerides of formula $R_x$—O—$CH_2$—CH(OR)—$CH_2$—O—$R_z$, according to the invention, wherein at least one of $R_x$, $R_y$ and/or $R_z$ is azelaic acid. The kinematic viscosity of the triglycerides mixture at 100° C. was 692 cSt.

After evaporation of the excess butyl alcohol and volatile butyl esters, a triglycerides mixture containing oligomeric structures was obtained with a Mn of about 1900 Da.

The weight ratio of the resulting mixture of triglycerides containing oligomeric structures to the evaporated volatile butyl esters fraction was only of about 50/50. The yield in was notably lower than that obtained with the process of the present invention.

The invention claimed is:

1. Process comprising the steps of:
   a) heating for a time of at least 10 minutes a starting mixture of one or more triglycerides containing saturated dicarboxylic acids, obtaining an intermediate mixture comprising said triglycerides in condensed form and one or more free dicarboxylic acids (condensation step);
   b) esterifying said intermediate mixture with monohydric alcohols, obtaining a reaction product comprising one or more oligomeric structures and one or more diesters of dicarboxylic acids (esterification step);
   c) separating said diesters of dicarboxylic acids from said reaction product, obtaining a final mixture of triglycerides comprising one or more oligomeric structures (separation step), wherein the said oligomeric structures have the following structure:

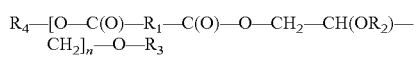

in which
   $R_1$ is selected from $C_2$-$C_{22}$ alkylenes,
   $R_2$ is selected from one or more of the following groups consisting of $C_6$-$C_{24}$ dicarboxylic acid residues and $C_6$-$C_{24}$ monocarboxylic acid residues,
   $R_3$ is selected from one or more of the following groups consisting of H, $C_6$-$C_{24}$ dicarboxylic acid residues and $C_6$-$C_{24}$ monocarboxylic acid residues,
   $R_4$ is an alkyl group,
   n is a whole number equal to or greater than 2,
   the said $C_6$-$C_{24}$ dicarboxylic acids of $R_2$ and $R_3$ being esterified with monoalcohols and the said mixture of triglycerides having a Number Average Molecular Weight (Mn) of between 800 and 10,000 Da.

2. Process according to claim 1 wherein said steps (a)-(c) are performed at temperatures below 250° C.

3. Process according to claim 1 wherein said condensation step (a) occurs at temperatures between 170° C. and 250° C.

4. Process according to claim 1 wherein said esterification step (b) is carried out without added catalyst or in the presence of acid catalysts consisting of one or more phosphorus compounds.

5. Process according to claim 4 wherein the said phosphorus compounds are selected from mineral acids containing phosphorus, their organic derivatives in which the acid is esterified with alcohols or their mixtures.

6. Process according to claim 4 wherein the said phosphorus compounds are selected from phosphoric acid, phosphonic acid, oligo- or polyphosphoric acids, condensation products of phosphoric acid, or their mixtures.

7. Process according to claim 1 wherein said esterification step (b) is carried out in the presence of acid catalysts consisting of one or more phosphorus compounds and at temperatures comprised between 50 and 200° C.

8. Process according to claim 4 wherein said esterification step (b) is carried out without added catalyst and at temperatures comprised between 100 and 250° C.

9. Process according to claim 1 wherein the monohydric alcohols of step b) are selected from aliphatic, linear or branched $C_1$-$C_{12}$ alcohols.

10. Process according to claim 1 wherein the starting mixture of step a) is obtained from oxidative cleavage of vegetable oils.

11. Process according to claim 10 wherein the starting mixture of step a) is obtained from oxidative cleavage of sunflower oil with a high oleic acid content.

12. Process according to claim 1 wherein said final mixture of triglycerides comprises monomeric triglycerides containing one or more $C_4$-$C_{24}$ saturated or unsaturated alkyl residues, linked to the glycerol molecule through ether linkages.

13. Process according to claim 1 wherein said final mixture of triglycerides comprises oligo-glycerols containing one or more $C_4$-$C_{24}$ saturated or unsaturated alkyl residues, linked to the glycerol molecule through ether linkages.

14. Process according to claim 1 wherein said final mixture of triglycerides comprises esters of saturated monocarboxylic acids, which contain one or more keto groups and/or secondary hydroxyl groups, with $C_1$-$C_{12}$ linear or branched monohydric alcohols.

15. Process according to claim 14, wherein said secondary hydroxyl groups are condensed with monocarboxylic acids and/or alkyl groups and/or with dicarboxylic acids esterified with $C_1$-$C_{12}$ linear or branched monohydric alcohols.

16. Process according to claim 1 wherein said separation step (c) is effected by distillation or by evaporation in a falling film evaporator or a thin film evaporator.

17. Process according to claim 2 wherein said condensation step (a) occurs at temperatures between 170° C. and 250° C.

18. Process according to claim 2 wherein said esterification step (b) is carried out without added catalyst or in the presence of acid catalysts consisting of one or more phosphorus compounds.

19. Process according to claim 3 wherein said esterification step (b) is carried out without added catalyst or in the presence of acid catalysts consisting of one or more phosphorus compounds.

20. Process according to claim 18 wherein the said phosphorus compounds are selected from mineral acids containing phosphorus, their organic derivatives in which the acid is esterified with alcohols or their mixtures.

* * * * *